United States Patent [19]
Stockhammer et al.

[11] Patent Number: 6,001,838
[45] Date of Patent: Dec. 14, 1999

[54] PROCESS FOR THE SEPARATION OF PYRIMIDINE DERIVATIVES FROM AQUEOUS SOLUTIONS

[75] Inventors: Stefan Stockhammer, Brusno; Wiltrud Treffenfeldt, Obertshausen; Andrea Preuss, Hanau, all of Germany

[73] Assignee: Degussa-Huls AG, Frankfurt, Germany

[21] Appl. No.: 09/040,308

[22] Filed: Mar. 18, 1998

[30] Foreign Application Priority Data

Mar. 18, 1997 [DE] Germany .............................. 197 11 082

[51] Int. Cl.⁶ .......................... A01N 43/54; C07D 239/02
[52] U.S. Cl. .......................... 514/256; 514/269; 544/298; 544/335
[58] Field of Search ..................... 514/256, 269; 544/298, 335

[56] References Cited

FOREIGN PATENT DOCUMENTS

| 0 553 884 A1 | 8/1993 | European Pat. Off. . |
| 42 44 580 A1 | 7/1994 | Germany . |
| 43 32 175 A1 | 3/1995 | Germany . |
| 44 27 617 A1 | 2/1996 | Germany . |

*Primary Examiner*—Mukund J. Shah
*Assistant Examiner*—Tamthom N. Truong
*Attorney, Agent, or Firm*—Pillsbury Madison & Sutro LLP

[57] ABSTRACT

A process for the separation and purification of pyrimidine derivatives, such as tetrahydropyrimidines, in particular 1,4,5,6-tetrahydro-2-methyl-4-pyrimidinecarboxylic acids (ectoine) from aqueous solutions by a combination of adsorption using inorganic solids and crossflow filtration.

17 Claims, 1 Drawing Sheet

PROCESS FOR THE SEPARATION OF PYRIMIDINE DERIVATIVES FROM AQUEOUS SOLUTIONS

CROSS-REFERENCE TO RELATED APPLICATION

This application claims priority from German Application No. 19711082.7, filed on Mar. 18, 1997, the subject matter of which is hereby incorporated herein by reference.

FIELD OF THE INVENTION

The invention relates to a process for the separation and purification of pyrimidine derivatives, particularly tetrahydropyrimidines, in particular 1,4,5,6-tetrahydro-2-methyl-4-pyrimidinecarboxylic acids (ectoines), from aqueous solutions by adsorption using zeolites in combination with cross filtration.

BACKGROUND OF THE INVENTION

The term tetrahydropyrimidine derivatives is used in particular to mean the compounds known from EP-A1-0553884.

Structurally, ectoines are cyclic amino acid derivatives, which belong to the class of so-called "compatible solutes". In high concentration they are also compatible with the cytoplasm and stabilize the cell components in an environment exhibiting low water activity. This action makes them suitable for a wide range of applications in the fields of medicine and cosmetics.

New biotechnological processes have made it possible to grow halophilic eubacteria, e.g. of the genus Halomonas, and to cause these organisms to excrete the ectoines into the medium surrounding them (T. Sauer et al., GIT Fachz. Lab. 10/95).

During subsequent processing, the ectoine is then purified by means of organic cation exchangers and crystallization.

However, it has become apparent that, for a suitable commercial product with approx. 90% purity to be obtained, this process has to comprise several stages and is very time consuming.

SUMMARY OF THE INVENTION

The object of the invention is to provide an alternative process comprising effective separation of the tetrahydropyrimidine derivatives according to EP-A1-0553884 and in particular ectoines from an aqueous solution, in particular a fermentation solution, possibly containing further organic compounds and purification of these pyrimidine derivatives, insofar as they may be adsorbed using zeolites.

The invention particularly provides a process for the separation and purification of pyrimidine derivatives, in particular tetrahydropyrimidines, in particular 1,4,5,6-tetrahydro-2-methyl-4-pyrimidinecarboxylic acids (ectoines) from aqueous solutions, characterized in that the aqueous solutions are brought into contact with a preferably acid zeolite with a modulus of from 15 to 1000 at a pH value of from 1.5 to 7.0, the surface-modified zeolite is isolated when adsorption is complete and the adsorbed derivatives are desorbed with an aqueous, in particular ammonium hydroxide-containing, solution adjusted to a pH value >8.0. The solution may also be adjusted to this pH value by the addition of a basic organic component, in particular lysine. (Modulus should be understood to mean the molar ratio of $SiO_2$ to $Al_2O_3$).

This process step may optionally be carried out repeatedly, depending on the level of purity required of the derivatives to be isolated.

This means that the solution obtained by desorption after the first desorption step is additionally once more or repeatedly brought into contact with suitable types of zeolite in the pH range suited to effective adsorption of the derivatives, the adsorbed derivatives being desorbed correspondingly frequently in the case of a repeated purification sequence.

DETAILED DESCRIPTION OF THE PREFERRED EMBODIMENTS

Figure 1:
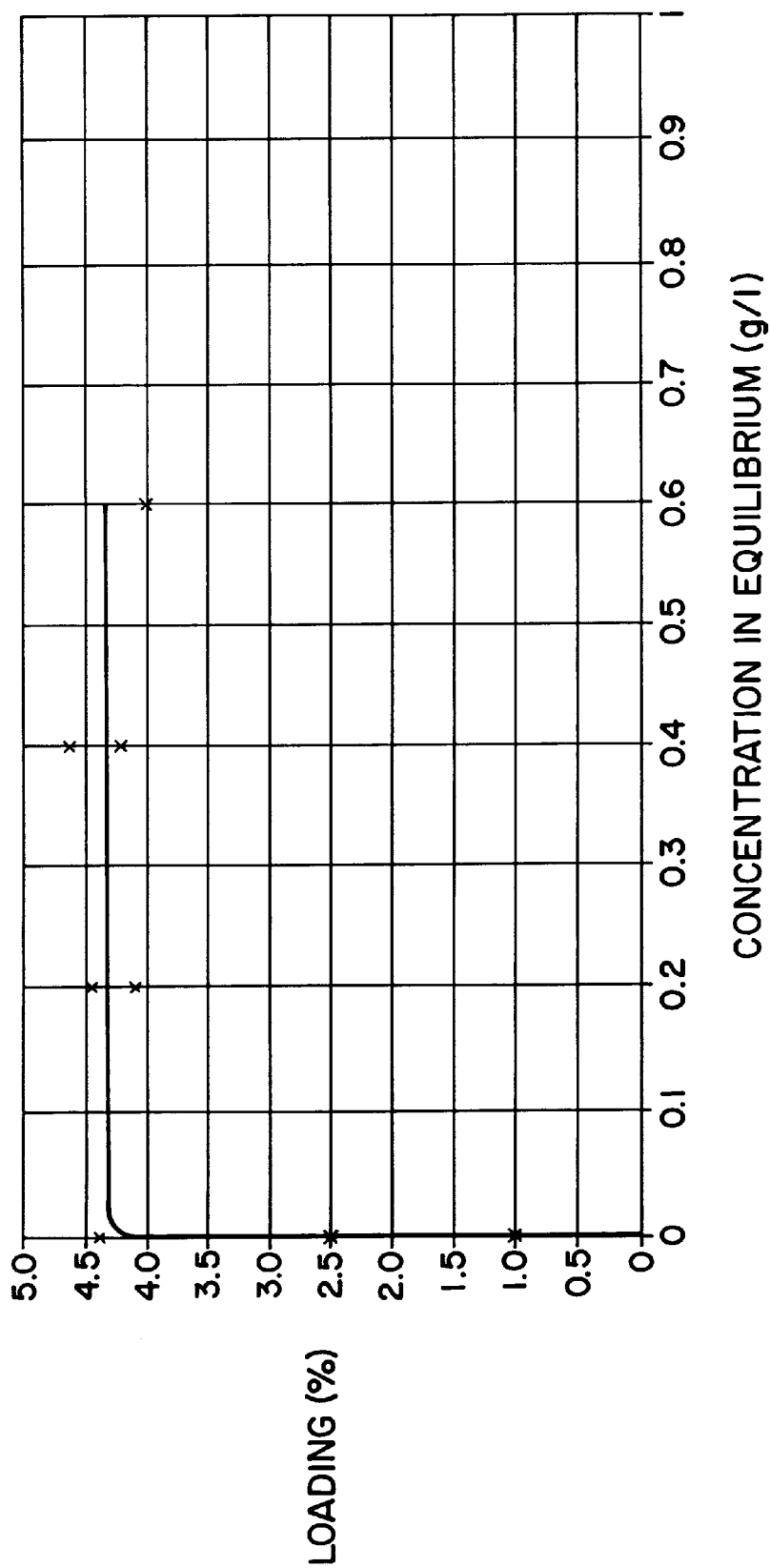
FIG. 1 shows an adsorption isotherm for ectoine using ZSM5 zeolite adsorbent.

The tetrahydropyrimidine derivatives to be separated and purified according to the invention are in particular compounds of the formula (I)

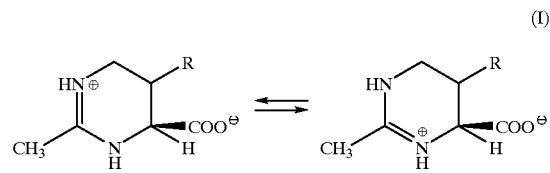

(I)

in which R means H or OH, in particular H, and the adsorbable tetrahydropyrimidine derivatives known from EP-A1-0533 884.

The solutions from which these and the ectoines according to formula (I) are to be separated are generally aqueous in nature.

The solutions to be purified are preferably obtained by fermentation with suitable bacteria. The pH value then has to be appropriately conformed to the adsorption conditions.

In a preferred embodiment, the micro-organisms are in this instance at least partially removed from the fermentation broth beforehand, in particular by centrifugation, but direct purification of the ectoines from the biomass-containing solution is also possible.

The ectoine is released from the cells by suitable decomposition methods (hypo-osmotic shock, mechanical or chemical cell decomposition).

The proteins which may disturb separation of the ectoines by adsorption are advantageously precipitated by suitable adjustment of the pH value and then removed.

Zeolites suitable for adsorption of the compounds to be separated according to the invention are those of the types Y, DAY, mordenite, dealuminized mordenite, ZSM-5, dealuminized ZSM-5, β or VPI5 and have a modulus of from 10 to 1000, in particular from 15 to 200, and preferably from 15 to 45. The ZSM-5 type is preferably used in the H, ammonium or Na form.

The process is carried within a temperature range of from 15 to 80° C.

In general, the concentration of ectoines may range up to the respective solubility limit in the aqueous medium, and in particular from 0.1 to 4.0 g/l. The adsorbents may be used in powdered form or as shaped particles, depending on the medium.

In an advantageous embodiment, adsorption is combined with crossflow filtration, wherein the solutions containing the tetrahydropyrimidine derivatives (A), in particular the ectoines, are brought into contact with suspensions of an acid zeolite and, after adsorption of these derivatives (A)

a) the zeolite thus loaded is caused to flow past a porous surface/membrane, wherein b) a difference in pressure is established between the side of the surface/membrane over which the zeolite flows and the opposite side thereof, such that c) part of the solution flowing over the surface/membrane and wholly or partially freed of derivatives flows through the surface/membrane perpendicularly to the flow direction (filtrate flow), d) the solution, which is free of the derivatives (A) but which may contain organic impurities, is separated in a washing step, and e) the adsorbed compounds are then desorbed.

The latter is effected at a suitable pH value, in particular at a pH value >8.0, or with a suitable solvent, e.g. methanol.

Adsorbents which are particularly suitable are fine-particle zeolite powders of the above-mentioned types with a particle diameter of from 1 to 100 μm, in particular 2 to 20 μm.

These are generally used in the form of aqueous suspensions with a solids content of from 5 to 60 wt.%, preferably from 20 to 50 wt.%.

Suitable filter surfaces are organic or ceramic membranes with ultra-, nano- or microfiltration properties.

If the process is carried out according to the invention, superficial layers resulting in high filtration resistances do not form on the filter medium. In this way, a problem is avoided which has to be solved, when this process is used in other applications, by additional cleaning cycles for the membrane used (DE-PS 43 32 175).

According to the invention, as early as in the first purification stage a product is surprisingly obtained which exhibits a purity of >70%, which may be increased to over 90% in a second similar purification stage.

To increase purity, the solutions obtained in the purification may be returned once or repeatedly to the purification process according to the invention. A variant of the process according to the invention includes combining the process with the purification, e.g. of ectoine solutions, known from the prior art, which uses organic cation exchangers and other purification steps. A corresponding adsorption and desorption step is effected before and/or after a purification stage by adsorption with one of the zeolites used according to the invention followed by desorption.

Example 1

Adsorption of ECTOINE from production solution: theoretical, multiple cycles

FIG. 1 shows an adsorption isotherm for ectoine using ZSM5 zeolite for adsorption, wherein loading % is charted against concentration in equilibrium (g/l).

While the invention has been described with respect to certain embodiments thereof, it will be appreciated that variations and modifications may be made without departing from the spirit and scope of the invention.

What is claimed is:

1. A process for the separation and purification of tetrahydropyrimidine derivatives from aqueous solutions, wherein the tetrahydropyrimidine derivatives have the structure of formula I

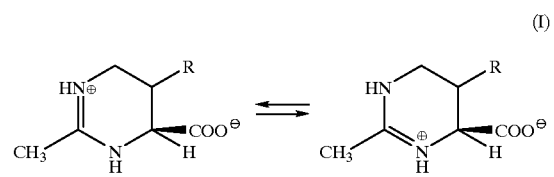

wherein R is hydrogen or hydroxy, comprising:

bringing the aqueous solution into contact with an acid zeolite;

adsorbing the derivatives on the acid zeolite at a first pH value; and when adsorption is complete, recovering the derivatives by desorption at a second, different, pH value.

2. A process according to claim 1, comprising:

bringing the aqueous solutions into contact with an acid zeolite with a modulus of from 15 to 1000 at a pH value of from 1.5 to 7.0 and, when adsorption is complete, desorbing the adsorbed derivatives with an aqueous solution optionally adjusted to a pH value >8.0 by the addition of a basic organic component.

3. A process according to claim 1, comprising:

separating 1,4,5,6-tetrahydro-2-methyl-4-pyrimidinecarboxylic acids from aquenous solutions.

|  | Prior to adosrption in the solution | | After adsorption in the solution | | on the adsorbent | After desorption in the solution | | Yield (%) per step |
|---|---|---|---|---|---|---|---|---|
|  | Conc. (g/l) | Purity (%) | Conc. (g/l) | Purity (%) | Purity (%) | Conc. (g/l) | Purity (%) |  |
|  | | | Total yield: 65% | | | | | |
| Remainder | 1.8 | 51.4 | 1.5 | 100 | 15 | 0.4 | 26 | |
| Ectoine | 1.7 | 48.6 | 0 | 0 | 85 | 1.11 | 74 | 65% |
|  | | | Total Yield: 42% | | | | | |
| Remainder | 0.4 | 33.3 | 0.33 | 100 | 6 | 0.07 | 9 | |
| Ectoine | 1.11 | 74 | 0 | 0 | 94 | 0.72 | 91 | 65% |

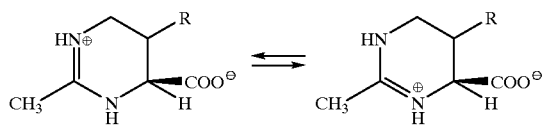
(I)

4. A process according to claim 1, comprising:
bringing the solution obtained by desorption into contact again with the zeolite;
desorbing the adsorbed derivates; and
optionally repeating both these steps at least once.

5. A process according to claim 1, comprising using a fermentation solution as the aqueous solution.

6. A process according to claim 5, comprising:
prior to adsorption, at least partially removing the microorganisms from the fermentation solution.

7. A process according to claim 5, comprising:
prior to adsorption, at least partially removing the soluble proteins from the fermentation solution.

8. A process according to claim 1, comprising:
using acid zeolites selected from the group consisting of Y, DAY, mordenite, dealuminized mordenite, ZSM-5, dealuminized ZSM-5, β or VPI-5, with a modulus of from 15 to 1000, as adsorbents.

9. A process according to claim 7, comprising:
using zeolites of ZSM5 or mordenite in H, ammonium or Na form.

10. A process according to claim 1, for separation of tetrahydropyrimidine derivatives, adsorbed using fine-particle zeolites, and wherein:
said process includes crossflow filtration, and
a) the zeolites are in the form of suspensions and, when loaded with the derivatives, flow past a porous surface/membrane, wherein
b) a difference in pressure is established between a first side of the surface/membrane over which the zeolites flow and an opposite, second side thereof, such that
c) part of the solution flowing over the surface/membrane and wholly or partially freed of the adsorbed derivatives flows through the surface/membrane perpendicularly to the flow direction,
d) separating the solution, which is free of the derivatives but which may contain organic impurities, in a washing step, and
e) desorbing the adsorbed derivatives.

11. A process according to claim 10, comprising using zeolites with an average particle diameter of from 1 to 100 βm.

12. A process according to claim 10, comprising:
establishing a transmembrane pressure of from 0.2 to 3 bar.

13. A process according to claim 10, comprising:
using ceramic or organic membrane/porous surfaces which exhibit ultrafiltration or micro- or nanofiltration properties.

14. A process according to claim 1 wherein the solution undergoes adsorption and desorption one or more times.

15. A process according to claim 1, further comprising:
purifying the desorbed pyrimidine derivatives using cation exchangers.

16. A process according to claim 10 wherein the solution undergoes adsorption and desorption one or more times.

17. A process according to claim 10, further comprising:
purifying the desorbed pyrimidine derivatives using cation exchangers.

* * * * *